United States Patent
Albert et al.

(10) Patent No.: US 7,799,812 B2
(45) Date of Patent: *Sep. 21, 2010

(54) REVERSE ISOXAZOLES

(75) Inventors: Rainer Albert, Basel (CH); Frederic Zecri, Bartenheim (FR)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/162,413

(22) PCT Filed: Jan. 25, 2007

(86) PCT No.: PCT/EP2007/000638

§ 371 (c)(1),
(2), (4) Date: Jul. 28, 2008

(87) PCT Pub. No.: WO2007/085451

PCT Pub. Date: Aug. 2, 2007

(65) Prior Publication Data

US 2009/0137636 A1    May 28, 2009

(30) Foreign Application Priority Data

Jan. 27, 2006    (GB)    ................... 0601744.6

(51) Int. Cl.
*A61K 31/4245*    (2006.01)
*A61K 31/42*    (2006.01)
*C07D 271/06*    (2006.01)
*C07D 261/08*    (2006.01)

(52) U.S. Cl. .................. 514/364; 514/378; 548/131; 548/247

(58) Field of Classification Search .................. None
See application file for complete search history.

(56) References Cited

FOREIGN PATENT DOCUMENTS

| EP | 1277744 A1 | 1/2003 |
|---|---|---|
| EP | 1491190 A1 | 12/2004 |
| EP | 1650199 A1 * | 4/2006 |
| WO | WO 00/15213 * | 3/2000 |
| WO | WO00/15213 A1 | 3/2000 |
| WO | WO03/035610 A1 | 5/2003 |
| WO | WO2004/103279 A2 | 12/2004 |
| WO | WO 2005/032465 * | 4/2005 |
| WO | WO2005/032465 A2 | 4/2005 |
| WO | WO2005/058848 A1 | 6/2005 |
| WO | WO2005/082089 A2 | 9/2005 |

OTHER PUBLICATIONS

Ettmayer et al. "Lessons Learned from Marketed and Investigational Prodrugs." J. Med. Chem., (2004), 47(10): 2393-2404.*
Morissette et al. "High-throughtput crystallization: polymorphs, salys, co-crystals and solvates of pharmaceutical solids." Advanced Drug Delivery Reviews, 56 (2004): 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Vippagunta et al. "Crystalline solids." Advanced Drug Delivery Reviews, 48 (2001): 3-26.*
Wolff et al. Burger's Medicinal Chemistry and Drug Discovery. 5th ed. vol. 1: Principles and Practice. pp. 975-977.*
Machine translation of WO 00/015213. Obtained from AIPN website. Accessed Jan. 18, 2010.*
Karamysheva et al., "Dependence of Mesomorphic Properties of 3;5-di-substituted 1,2,4-oxidiazoles on Geometric and Electronic Factors", Molecular Crystals and Liquid Crystals, 1995 vol. 260 pp. 217-225.
Li et al., "Discovery of Potent 3,5-Diphenyl-1,2,4-oxadiazole Sphingosine-1-phosphate-1 (S1P1) Receptor Agonists with Exceptional Selectivity against S1P2 and S1P3", Journal of Medicinal Chemistry, vol. 48 No. 20 pp. 6169-6173.

* cited by examiner

*Primary Examiner*—Golam M. M. Shameem
*Assistant Examiner*—Alicia L Fierro
(74) *Attorney, Agent, or Firm*—Hoxie & Associates LLC

(57) ABSTRACT

The present invention relates to polycyclic compounds, processes for their production, their use as pharmaceuticals and to pharmaceutical compositions comprising them.

7 Claims, No Drawings

REVERSE ISOXAZOLES

This application is a U.S. National Phase filing of International Application Ser. No. PCT/EP2007/000638 filed 25 Jan. 2007, and claims priority to G.B. application Ser. No. 0601744.6 filed 27 Jan. 2006, the contents of which are incorporated herein by reference in their entirety.

The present invention relates to polycyclic compounds, processes for their production, their use as pharmaceuticals and to pharmaceutical compositions comprising them.

More particularly the present invention provides in a first aspect a compound of formula I

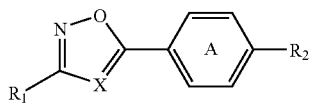

I wherein either X is —N= or =CH—;

$R_1$ is substituted biphenylyl, 4-phenoxy-phenyl or 4-(phenyl-$C_{1-4}$alkoxy)-phenyl wherein at least one of the phenyl groups is monosubstituted, phenyl substituted by one or more substituents or substituted 5 or 6-membered heteroaryl;

wherein the substituents in each of the above are independent from each other selected from $C_{1-8}$alkyl, halo$C_{1-8}$alkyl, $C_{1-8}$alkoxy, halo$C_{1-8}$alkoxy, $C_{1-8}$alkoxy-$C_{1-8}$alkoxy, $C_{1-8}$alkyl-$C_{1-8}$alkoxy, $C_{1-8}$alkyl-halo$C_{1-8}$alkoxy, halo$C_{1-8}$alkyl-$C_1$-alkoxy, halo$C_{1-8}$alkyl-halo$C_{1-18}$alkoxy, halo$C_{1-8}$alkoxy-$C_{1-8}$alkoxy, $C_{1-8}$alkoxy-1-halo$C_{1-8}$alkoxy, halo$C_{1-8}$alkoxy-halo$C_{1-8}$alkoxy, $C_{1-8}$alkoxy-$C_{1-8}$alkyl, halo$C_{1-8}$alkoxy-$C_{1-8}$alkyl, $C_{1-8}$alkoxy-halo$C_{1-8}$alkyl, halo$C_{1-8}$alkoxy-halo$C_{1-8}$alkyl, $C_{2-6}$alkenyloxy, $C_{2-6}$alkynyloxy, $C_{3-6}$cycloalkyl, $C_{3-6}$cycloalkyl-$C_{1-4}$alkyl, $C_{3-6}$cycloalkyl-$C_{1-4}$ alkoxy, $C_{3-4}$cycloalkyl-oxy, phenyl-$C_{1-4}$alkoxy and heterocyclic-$C_{1-4}$alkoxy;

$R_2$ is $C_{1-4}$ alkyl optionally substituted by halogen, OH, $NH_2$, $C_{1-4}$alkoxy or $C_{1-4}$alkylcarbonyloxy; amino; OH; $C_{1-4}$alkoxy; NH—OH; carboxy; sulfamoyl; carbamoyl; or HN—CO—$C_{1-4}$alkyl; or $R_2$ is $R_3$-$R_4$—COOH or $R_3$-$R_4$—$CONH_2$ wherein $R_3$ is $SO_2$—NH, $SO_2$—N($C_{1-4}$alkyl), CO—NH, CO—N($C_{1-4}$alkyl), $CH_2$—O, NH—CO, or N($C_{1-4}$alkyl)CO; and $R_4$ is $C_{1-6}$alkylene optionally interrupted by O, S or C=$CH_2$ or optionally substituted phenylene or $C_{3-6}$cycloalkylene; and Ring A may be phenyl or heteroaryl, each being optionally further substituted by one or more substituents independently selected from halogen, $C_{1-4}$alkyl, halo$C_{1-4}$alkyl, $C_{1-4}$alkoxy, halo$C_{1-4}$alkoxy or nitrile; or $R_2$ is hydrogen under the proviso that Ring A is 3-pyridyl;

or a physiologically hydrolysable derivative thereof, a salt, hydrate and/or solvate thereof.

Halogen may be fluorine, chlorine or bromine, preferably fluorine or chlorine. Alkyl or alkoxy as a group or present in a group may be straight or branched. $C_{1-6}$alkylene may be straight or branched.

Halo$C_{1-8}$alkyl or halo$C_{1-8}$alkoxy as a group or a moiety present in a group may be $C_{1-8}$alkyl or $C_{1-8}$alkoxy substituted by 1 to 5 halogen, e.g. $CF_3$ or $CF_3$—$CH_2$—O—. $C_{1-8}$alkyl-halo$C_{1-8}$alkoxy may be halo$C_{1-8}$alkoxy further substituted by $C_{1-4}$alkyl, e.g. in position 1. The same may apply to the other groups.

When $R_1$ is substituted biphenylyl, 4-phenoxy-phenyl or 4-(phenyl-$C_{1-4}$alkoxy)-phenyl, either one and/or both phenyl moieties may be substituted, e.g. mono- or di-substituted e.g. by halogen, $C_{1-4}$alkyl, $C_{1-4}$alkoxy, halo$C_{1-18}$alkyl, halo$C_{1-8}$alkoxy or nitrile. Preferably at least one phenyl moiety of the biphenylyl, 4-phenoxy-phenyl or 4-(phenyl-$C_{1-4}$alkoxy)-phenyl is monosubstituted, e.g. as indicated above. More preferably each phenyl moiety of the biphenylyl, 4-phenoxy-phenyl or 4-(phenyl-$C_{1-4}$alkoxy)-phenyl is monosubstituted, e.g. as indicated above, e.g. by halo$C_{1-8}$alkyl, and optionally as substitutent on the second phenyl moiety either halogen, $C_{1-4}$alkyl or $C_{1-4}$alkoxy or halo$C_{1-8}$alkyl.

When $R_1$ is substituted phenyl, it may be mono- or di-substituted. When $R_1$ is mono-substituted phenyl, said substituent may preferably be halo$C_{1-8}$alkyl, in particular being in meta position, especially representing trifluoromethyl in meta position. When $R_1$ is disubstituted phenyl, one substituent may preferably be halo$C_{1-8}$alkyl, in particular trifluoromethyl, and the second substitutent may be $C_{1-8}$alkyl, halo$C_{1-8}$ alkyl, $C_{1-8}$alkoxy, halo$C_{1-8}$alkoxy, $C_{1-8}$alkoxy-$C_{1-8}$alkoxy, $C_{1-8}$alkyl-$C_{1-8}$alkoxy, $C_{1-8}$alkyl-halo$C_{1-8}$alkoxy, halo$C_{1-8}$alkyl-$C_{1-8}$alkoxy, halo$C_{1-8}$alkyl-halo$C_{1-8}$alkoxy, halo$C_{1-8}$alkoxy-$C_{1-8}$alkoxy, $C_{1-8}$alkoxy-halo$C_{1-8}$alkoxy, halo$C_{1-8}$alkoxy-halo$C_{1-8}$alkoxy, $C_{1-8}$alkoxy-$C_{1-8}$alkyl, halo$C_{1-8}$alkoxy-$C_{1-8}$alkyl, $C_{1-8}$alkoxy-halo$C_{1-8}$alkyl, halo$C_{1-8}$alkoxy-halo$C_{1-8}$alkyl, $C_{2-6}$alkenyloxy, $C_{2-6}$alkynyloxy, $C_{3-6}$cycloalkyl, $C_{3-6}$cycloalkyl-$C_{1-4}$alkyl, $C_{3-6}$cycloalkyl-$C_{1-4}$ alkoxy, $C_{3-6}$cycloalkyl-oxy, phenyl-$C_{1-4}$alkoxy or heterocyclic-$C_{1-4}$alkoxy, preferably $C_{1-8}$alkyl, halo$C_{1-8}$alkyl, $C_{1-8}$alkoxy, halo$C_{1-8}$alkoxy or $C_{3-6}$cycloalkyl, more preferably $C_{1-8}$alkyl, halo$C_{1-8}$alkyl, $C_{1-8}$alkoxy or $C_{3-6}$cycloalkyl, and in particular $C_{3-6}$cycloalkyl. When $R_1$ is disubstituted phenyl the first substituent is preferably in meta and the second preferably in para position.

Examples of a 5 or 6-membered heteroaryl as $R_1$ include e.g. thienyl or furyl. Preferred is thienyl. When $R_1$ is substituted heteroaryl, it is mono- or disubstituted, preferably disubstituted. The substituent(s) may be e.g. halo$C_{1-8}$alkyl, e.g. $CF_3$, and/or phenyl optionally substituted by halogen, $C_{1-4}$alkyl or $C_{1-4}$alkoxy.

When $R_4$ is optionally substituted phenylene or $C_{3-6}$cycloalkylene, it may be 1,4-phenylene or $C_{3-6}$cycloalkylene, e.g. cyclohexylene, optionally substituted by halogen.

Ring A may optionally be further substituted, e.g. by halogen, $C_{1-4}$alkyl, halo$C_{1-4}$alkyl, $C_{1-4}$alkoxy, halo$C_{1-4}$alkoxy or nitrile, preferably by halogen, $C_{1-4}$alkyl, halo$C_{1-4}$alkyl, $C_{1-4}$alkoxy, or halo$C_{1-4}$alkoxy, more preferably by halogen, $C_{1-4}$alkyl, halo$C_{1-4}$alkyl, or $C_{1-4}$alkoxy, and especially by halogen, $C_{1-4}$alkyl or $C_{1-4}$alkoxy. When Ring A is heteroaryl, it may be a 6-membered aromatic ring comprising one heteroatom selected from nitrogen, oxygen and sulfur, e.g. pyridyl, pyrimidinyl or pyrazinyl. When Ring A is heteroaryl it may be preferably pyrimidinyl or pyridyl, more preferably pyridyl, even more preferably 3-pyridyl.

The following significances are preferred independently, collectively or in any combination or sub-combination:

i) $R_1$ is biphenylyl, 4-phenoxy-phenyl or 4-(phenyl-$C_{1-4}$alkoxy)-phenyl wherein at least one of the phenyl groups bears a halo$C_{1-4}$alkyl, e.g. $CF_3$;

ii) $R_1$ is phenyl substituted by halo$C_{1-4}$alkyl, e.g. $CF_3$ and optionally by a second substituent as indicated above:

iii) $R_1$ is thienyl substituted by halo$C_{1-4}$alkyl, e.g. $CF_3$, and phenyl;

iv) $R_2$ is sulfamoyl;

v) $R_2$ is $R_3$-$R_4$—COOH; or $R_3$-$R_4$—$CONH_2$; more preferably $R_3$-$R_4$—$CONH_2$;

vi) $R_3$ is $SO_2$—NH; $SO_2$—N($C_{1-4}$alkyl); NH—CO; or N($C_{1-4}$alkyl)CO;

vii) $R_4$ is $C_{1-6}$alkylene optionally interrupted by O;

viii) $R_2$ is $NH_2$;

ix) Ring A is unsubstituted phenyl (i.e. no further substituent in addition to $R_2$).

x) Ring A is substituted or unsubstituted (i.e. no further substituent in addition to $R_2$) pyridyl.

The compounds of formula I may exist in free form or in salt form, e.g. addition salts with e.g. organic or inorganic acids, for example, hydrochloric acid or acetic acid, or salts obtainable when $R_2$ is or comprises COOH, with a base, e.g. alkali salts such as sodium or potassium, or substituted or unsubstituted ammonium salts.

It will be appreciated that the compounds of formula I may exist in the form of optical isomers, racemates or diastereoisomers. For example, $R_4$ may comprise an asymmetric carbon atom when $R_4$ is branched alkylene. It is to be understood that the present invention embraces all enantiomers and conformers and their mixtures. Similar considerations apply in relation to starting materials exhibiting asymmetric carbon atoms as mentioned above.

By a physiologically hydrolysable derivative of a compound of formula I is meant a compound which is hydrolysable under physiological conditions to yield a compound of formula I and a by-product which is itself physiologically acceptable, e.g. an ester which is hydrolyzed to yield a compound of formula I and a non-toxic alcohol at the desired dosage levels.

The present invention also includes a process for the production of a compound of formula I, which process comprises a) for the production of a compound of formula I wherein X is —N═ and $R_2$ is as defined above, reacting a compound of formula II

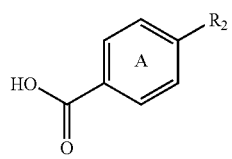

II wherein ring A and $R_2$ are as defined above, or a functional derivative thereof, e.g. an activated ester, acyl chloride or anhydride with a compound of formula III

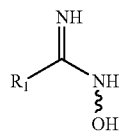

III wherein $R_1$ is as defined above or a functional derivative thereof; or b) for the production of a compound of formula I wherein X is CH and $R_2$ is $NH_2$ reacting a compound of formula VI

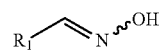

VI wherein $R_1$ is as defined above, with a compound of formula VII

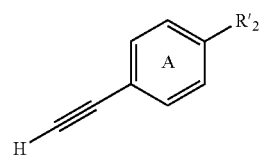

VII wherein Ring A is as defined above and $R'_2$ is $NH_2$; or c) converting a compound of formula I into another compound of formula I, and recovering the resulting compound of formula I in free form or in form of a salt, and, where required converting the compound of formula I obtained in free form into the desired salt form or vice versa.

The process steps a) to c) may be performed according to methods known in the art, or as disclosed below in the Examples.

Examples of conversion of a compound of formula I into another compound of formula I may include e.g.

i) For the production of a compound of formula I wherein $R_1$ is substituted biphenylyl, 4-phenoxy-phenyl or 4-(phenyl-$C_{1-4}$alkoxy)-phenyl wherein at least one of the phenyl groups is monosubstituted, converting a compound of formula I wherein $R_1$ is other than substituted biphenylyl, 4-phenoxy-phenyl or 4-(phenyl-$C_{1-4}$alkoxy)-phenyl wherein at least one of the phenyl groups is monosubstituted, into a compound of formula I wherein $R_1$ is substituted biphenylyl, 4-phenoxy-phenyl or 4-(phenyl-$C_{1-4}$ alkoxy)-phenyl wherein at least one of the phenyl groups is monosubstituted.

ii) For the production of a compound of formula I wherein $R_2$ is $R_3$-$R_4$—COOH, hydrolyzing a compound of formula I wherein the COOH present in $R_2$ is in form of a physiologically hydrolysable ester, e.g. a methyl ester.

iii) For the production of a compound of formula I wherein X is —N═ and Y is O and $R_2$ is $R_3$-$R_4$—COOH wherein $R_3$ is NH—CO or N($C_{1-4}$alkyl)CO and $R_4$ is as defined above, reacting a compound of formula I

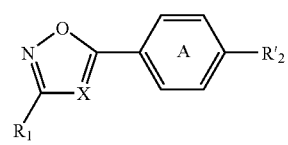

I wherein $R_1$, X, $R'_2$ and ring A are as defined above, with an acylating agent.

iv) For the production of a compound of formula I wherein $R_2$ is $R_3$-$R_4$—$CONH_2$, reacting a compound of formula I wherein $R_2$ is $R_3$-$R_4$—COOH with an amidating agent.

The compound of formula III used as starting material in process step a) may be obtained by reacting a compound of formula VIII

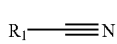

wherein $R_1$ is as defined above, with hydroxylamine.

The compound of formula VI used as starting material in process step b) may be produced by reacting a compound of formula IX

wherein $R_1$ is as defined above, with hydroxylamine.

A compound of formula I wherein X is —N═ and $R_2$ is $NH_2$ may also be produced by reacting a compound of formula III with a compound of formula II'

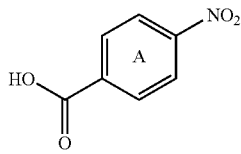

wherein Ring A is as defined above, or a functional derivative thereof, e.g. an activated ester, acyl chloride or anhydride. The nitro group present in the resulting compound may then be reduced, e.g. by catalytic hydrogenation.

Insofar as the production of the starting materials is not particularly described, the compounds are either known or may be prepared analogously to methods known in the art or as disclosed hereinafter.

The following Examples are illustrative of the invention.

EXAMPLE 1

4-[3-(2-trifluoromethyl-biphenyl-4-yl)-isoxazol-5-yl]-phenylamine

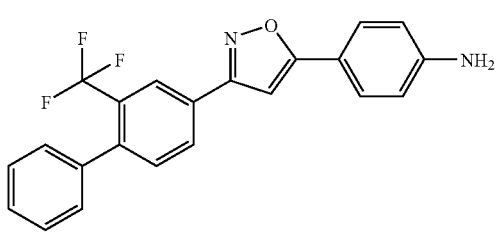

a) 2-Trifluoromethyl-biphenyl-4-carbaldehyde oxime

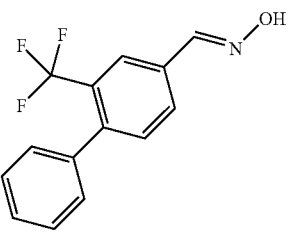

Step a) To a solution of 4-cyano-2-trifluoroaniline (1 eq) in benzene there is added under inert atmosphere n-pentylnitrite (1 eq) at 50° C. After one hour refluxing a second equivalent of n-pentylnitrite is added. After additional two hours of refluxing the reaction mixture is cooled to room temperature and concentrated under reduced pressure. The dark residue is purified on silica gel using c-hexane→hexane/ethyl acetate 9/1 as mobile phase (pale orange oil).

Step b) The compound of step a) (1 eq) is dissolved in formic acid (75%) and Ra—Ni (4 eq) is added. After 3 hours at 80° C. the reaction mixture is filtered through Hyflo Super Cel® and the catalyst/Hyflo is washed 2 times with ethanol (with caution→flammable). The resulting solution is concentrated (yield 61%; mixture of ester & acid) and is used for step c) without any further purification.

Step c) The compound of step b) and hydroxylamine hydrochloride (1.25 eq) are dissolved in ethanol and $K_2CO_3$ (1.1 eq) is added. After 18 hours at room temperature the reaction mixture is concentrated and after addition of water extracted with ethyl acetate. Purification is achieved, after drying over $Na_2SO_4$ over silica gel using c-hexane/ethyl acetate 9/1 as mobile phase, yielding 2-trifluoromethyl-biphenyl-4-carbaldehyde oxime.

ESI-MS (ESI$^+$): 266 (M+1H)$^+$ b) 4-[3-(2-Trifluoromethyl-biphenyl-4-yl)-isoxazol-5-yl]-phenylamine To a solution of 2-trifluoromethyl-biphenyl-4-carbaldehyde oxime (1 eq) in $CH_2Cl_2$ a 10% aqueous solution of NaOCl is added at 0° C. Thereafter a solution of 4-ethynylaniline (1.1 eq) is added and then the reaction mixture is stirred at room temperature for 16 hours. The reaction mixture is diluted with $CH_2Cl_2$ and 3 times extracted with water. The combined organic layers are dried over $Na_2SO_4$, filtered and concentrated. Purification is achieved, after drying over $Na_2SO_4$, over silica gel using c-hexane/ethyl acetate 9/1→7/3 as mobile phase.

ESI-MS (ESI$^+$): 381 (M+1H)$^+$

EXAMPLE 2

N-{4-[3-(2-trifluoromethyl-biphenyl-5-yl)-isoxazol-3-yl]-phenyl}-succinamic acid

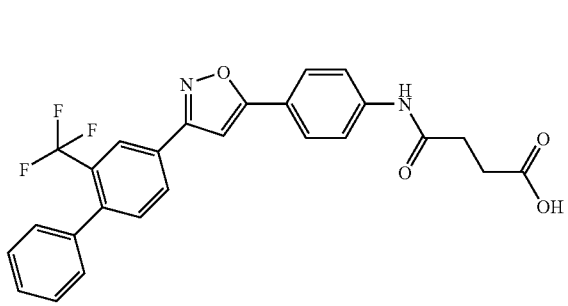

The compound (1 eq) of Example 1 is dissolved in CH$_2$Cl$_2$ and 4-methylmorpholine (2 eq) and succinic anhydride (2 eq) are added. After 16 hours at room temperature pure title product is obtained after filtration (white solid).

ESI-MS (ESI$^+$): 481 (M+1H)$^+$

EXAMPLE 3

N-{4-[3-(2-trifluoromethyl-biphenyl-4-yl)-isoxazol-5-yl]-phenyl}-succinamide

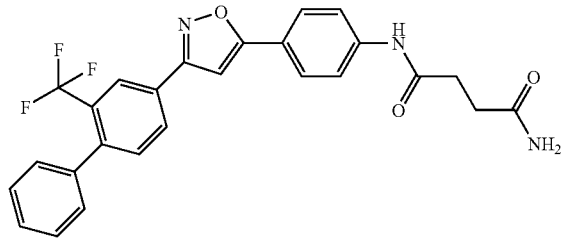

The compound of Example 2 is dissolved in DMF and subsequently N-(3-dimethylaminopropyl)-N'-ethylcarbodiimide hydrochloride (EDC.HCl; 1.5 eq), hydroxybenzotriazole (HOBt; 1.3 eq), NH$_4$OH 25% in water (1.2 eq) and diisopropylethylamine (1.5 eq) are added. After 16 hours at room temperature the reaction mixture is concentrated and purified on silica gel (CH$_2$Cl$_2$/methanol 95/5→CH$_2$Cl$_2$/methanol/acetic acid$_{50\%}$ 90/10/0.125 as mobile phase) resulting in pure title compound.

ESI-MS (ESI$^+$): 480 (M+1H)$^+$

EXAMPLE 4

3-{4-[3-(2-Trifluoromethyl-biphenyl-4-yl)-[1,2,4]oxadiazol-5-yl]-benzene-sulfonylamino}-propionic acid

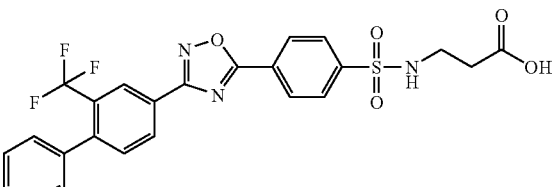

a) N-Hydroxy-2-trifluoromethyl-biphenyl-4-carboxamidine

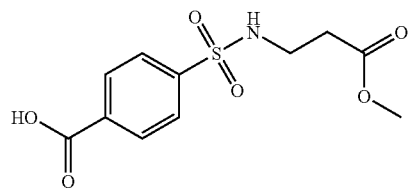

Step a) To a solution of 4-cyano-2-trifluoroaniline (1 eq) in benzene there is added under inert atmosphere n-pentylnitrite (1 eq) at 50° C. After one hour refluxing a second equivalent of n-pentylnitrite is added. After additional two hours of refluxing the reaction mixture is cooled to room temperature and concentrated under reduced pressure. The dark residue is purified on silica gel using c-hexane→c-hexane/ethyl acetate 9/1 as mobile phase (pale orange oil).

Step b) The compound of step a) is dissolved in THF and hydroxylamine (50% in water; 10 eq) is added dropwise at −10° C. After 16 hours at room temperature the reaction mixture is diluted with water and extracted with ethyl acetate. After drying of the organic phase with Na$_2$SO$_4$ purification is achieved on silica gel with c-hexane/ethyl acetate 75/25 as mobile phase.

b) 4-(2-Methoxycarbonyl-ethylsulfamoyl)-benzoic acid

It is obtained by reacting 4-chlorosulfonyl-benzoic acid (1 eq) with H-βAla-OMe×HCl in CH$_2$Cl$_2$ using diisopropylethylamine (2 eq) as base. After 30 minutes at room temperature the reaction mixture is extracted with water and the organic layer is dried over Na$_2$SO$_4$. Removal of the solvent gives the title compound.

c) 3-{4-[3-(2-Trifluoromethyl-biphenyl-4-yl)-[1,2,4]oxadiazol-5-yl]-benzenesulfonylamino}-propionic acid methyl ester 4-(2-Methoxycarbonyl-ethylsulfamoyl)-benzoic acid (1 eq) is dissolved in DMF and EDC.HCl (1.3 eq) and HOBt (1.1 eq) are added. After 30 minutes at room temperature N-hydroxy-2-trifluoromethyl-biphenyl-4-carboxamidine (1 eq) is added and the reaction mixture is kept at 90° C. for 16 hours. After removal of the solvent the residue is dissolved in ethyl acetate and extracted with saturated NaHCO$_3$ solution. Title compound is obtained after drying of the organic phase over Na$_2$SO$_4$ on silica gel using c-hexane/ethyl acetate/CH$_2$Cl$_2$ 8/2/1 as mobile phase.

ESI-MS (ESI$^-$): 530 (M−1H)$^-$ d) 3-{4-[3-(2-Trifluoromethyl-biphenyl-4-yl)-[1,2,4]oxadiazol-5-yl]-benzene-sulfonylamino}-propionic acid

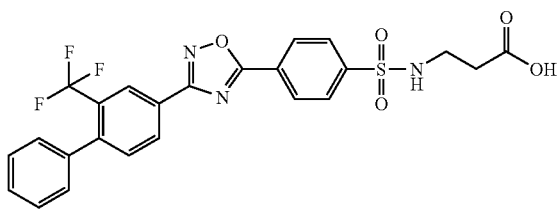

LiOH (2 eq) is dissolved in methanol/water (1/1) and the ester (1 eq) is added. After 4 hours at 50° C. methanol is removed under reduced pressure, the pH is adjusted to ~3 with 1N HCl and the reaction mixture is 3 times extracted with ethyl acetate. The combined organic layers are dried over Na$_2$SO$_4$, filtered, concentrated and the title compound is obtained as a white powder after removal of the solvent.

ESI-MS (ESI$^-$): 516 (M−1H)$^-$

EXAMPLE 5

4-[3-(2-Trifluoromethyl-biphenyl-4-yl)-[1,2,4]oxadiazol-5-yl]-phenylamine

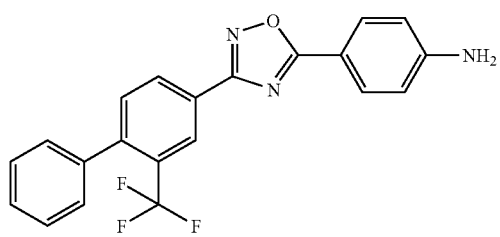

a) 5-(4-Nitro-phenyl)-3-(2-trifluoromethyl-biphenyl-4-yl)-[1,2,4]oxadiazole

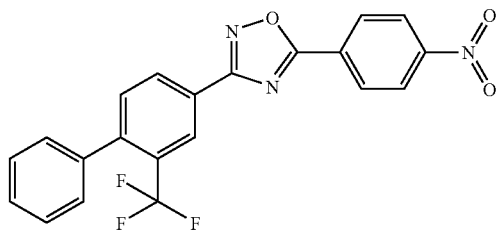

It is obtained as a white powder using 4-nitrobenzoic acid instead of 4-(2-methoxycarbonyl-ethylsulfamoyl)-benzoic acid in the procedure of Example 1—step c).

ESI-MS (ESI$^+$): 412 (M+1H)$^+$ b) The compound of step a) is dissolved in methanol/ethyl acetate 1/1 and hydrogenated at room temperature under normal pressure for 16 hours with Pd/C$_{10\%}$ as catalyst. After filtration through Hyflo Super Cel® the reaction mixture is concentrated and purified on silica gel (CH$_2$Cl$_2$→CH$_2$Cl$_2$/methanol 95/5 as mobile phase), yielding the title compound.

ESI-MS (ESI$^+$): 382 (M+1H)$^+$

EXAMPLE 6

2,6-Dimethoxy-3-[3-(2-trifluoromethyl-biphenyl-4-yl)-[1,2,4]oxadiazol-5-yl]-pyridine

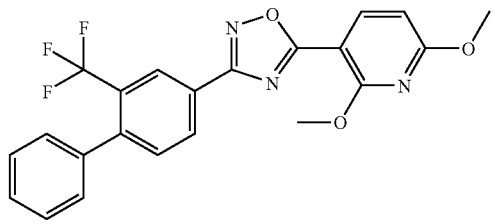

2,6-Dimethoxy-nicotinic acid (1 eq) is dissolved in dioxane and EDC.HCl (1.3 eq) and HOBt (1.1 eq) are added. After 30 minutes at room temperature N-hydroxy-2-trifluoromethyl-biphenyl-4-carboxamidine (1 eq) is added and the reaction mixture is kept at 900 degrees Celsius for 16 hours. After removal of the solvent the residue is dissolved in ethyl acetate and extracted with saturated NaHCO$_3$ solution. Title compound is obtained after drying of the organic phase over Na$_2$SO$_4$ on silica gel using c-hexane/ethyl acetate→c-hexane/ethyl acetate 100→70/30 as mobile phase.

ESI-MS (ESI$^-$): 426 (M−1H)$^-$

By following the procedure as described in the foregoing Examples and using the appropriate starting materials, the compounds of formula I

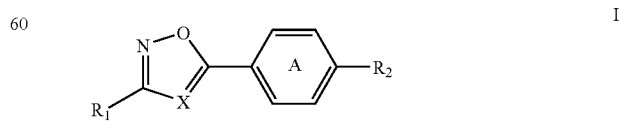

I wherein X, R$_1$, R$_2$ and Ring A are as defined in Table 1 below, are obtained.

TABLE 1

| Ex | R₁ | X | R₂ | Ring A | ESI + MS: |
|---|---|---|---|---|---|
| 7 | 2-CF$_3$-4-biphenylyl | CH | HN—CO—CH$_2$—C(CH$_3$)$_2$—COOH | phenyl | 509 (M + 1H)⁺ |
| 8 | 2-CF$_3$-4-biphenylyl | CH | HN—CO—CH$_2$—C(CH$_3$)$_2$—CONH$_2$ | phenyl | 508 (M + 1H)⁺ |
| 9 | 3-CF$_3$-4-cyclohexyl-phenyl | CH | NH$_2$ | phenyl | 387 (M + 1H)⁺ |
| 10 | 3-CF$_3$-4-cyclohexyl-phenyl | CH | HN—CO—CH$_2$—CH$_2$—COOH | phenyl | 487 (M + 1H)⁺ |
| 11 | 3-CF$_3$-4-cyclohexyl-phenyl | CH | HN—CO—CH$_2$—CH$_2$—CONH$_2$ | phenyl | 486 (M + 1H)⁺ |
| 12 | 2-CF$_3$-4-biphenylyl | N | SO$_2$—NH—CH$_2$—CH$_2$—CONH$_2$ | phenyl | 515 (M − 1H)⁻ |
| 13 | 2-CF$_3$-4-biphenylyl | N | SO$_2$—NH$_2$ | phenyl | 444 (M − 1H)⁻ |
| 14 | 2-CF$_3$-4-biphenylyl | N | OH | phenyl | 383 (M − 1H)⁻ |
| 15 | 2-CF$_3$-4-biphenylyl | N | OH | 3-CF$_3$-phenyl | 451 (M − 1H)⁻ |
| 16 | 2-CF$_3$-4-biphenylyl | N | HN—CO—CH$_2$—CH$_2$—COOH | phenyl | 480 (M − 1H)⁻ |
| 17 | 2-CF$_3$-4-biphenylyl BHT482 | N | HN—CO—CH$_2$—C(CH$_3$)$_2$—COOH | phenyl | 508 (M − 1H)⁻ |
| 18 | 2-CF$_3$-4-biphenylyl | N | HN—CO—CH$_2$—CH$_2$—CONH$_2$ | phenyl | 479 (M − 1H)⁻ |
| 19 | 2-CF$_3$-4-biphenylyl | N | HN—CO—CH$_2$—C(CH$_3$)$_2$—CONH$_2$ | phenyl | 507 (M − 1H)⁻ |
| 20 | 3-CF$_3$-4-cyclohexyl-phenyl | N | NH$_2$ | phenyl | 388 (M + 1H)⁺ |
| 21 | 3-CF$_3$-4-cyclohexyl-phenyl | N | HN—CO—CH$_2$—CH$_2$—COOH | phenyl | 488 (M + 1H)⁺ |
| 22 | 3-CF$_3$-4-cyclohexyl-phenyl | N | HN—CO—CH$_2$—CH$_2$—CONH$_2$ | phenyl | 487 (M + 1H)⁺ |
| 23 | 2-CF$_3$-4-biphenylyl | N | H | 3-pyridyl | 368 (M + 1H)⁺ |
| 24 | 2-CF$_3$-4-biphenylyl | N | NH$_2$ | 3-pyridyl | 383 (M + 1H)⁺ |
| 25 | 2-CF$_3$-4-biphenylyl | N | OH | 3-pyridyl | 384 (M + 1H)⁺ |
| 26 | 2-CF$_3$-4-biphenylyl | N | NH—OH | 3-pyridyl | 399 (M + 1H)⁺ |
| 27 | 2-CF$_3$-4-biphenylyl | N | HN—CO—CH$_2$—CH$_2$—COOH | 3-pyridyl | 483 (M + 1H)⁺ |
| 28 | 2-CF$_3$-4-biphenylyl | N | COOH | 3-pyridyl | 412 (M + 1H)⁺ |
| 29 | 3-CF$_3$-4-cyclohexyl-phenyl | N | COOH | 3-pyridyl | 418 (M + 1H)⁺ |
| 30 | 2-CF$_3$-4-biphenylyl | N | COOH | 2-pyridyl | 412 (M + 1H)⁺ |
| 31 | 2-CF$_3$-4-biphenylyl | N | CH$_2$—NH$_2$ | phenyl | 396 (M + 1H)⁺ |

The compounds of formula I in free form or in pharmaceutically acceptable salt form, exhibit valuable pharmacological properties, e.g. as S1P1 receptor agonists, e.g. as indicated in in vitro and in vivo tests and are therefore indicated for therapy.

A. In vitro

The compounds of formula I have binding affinity to individual human S1P receptors as determined in following assays:

A. In vitro: GPCR Activation Assay Measuring GTP [γ-$^{35}$S] Binding to Membranes Prepared from CHO Cells Expressing Human EDG Receptors S1P$_1$ (EDG-1) GTP [γ-$^{35}$S] binding assay: Homogenized membranes are prepared from CHO cell clones stably expressing a human EDG-1 N-terminal c-myc tag. Cells are grown in suspension in two 850 cm² roller bottles for three or fours days before harvesting. The cells are centrifuged down, washed once with cold PBS, and resuspended in ≦20 ml of Buffer A (20 mM HEPES, pH 7.4, 10 mM EDTA, EDTA-free complete protease inhibitor cocktail [1 tablet/25 ml]). The cell suspension is homogenized on ice, using a Polytron homogenizer at 30000 rpm at three intervals of 15 seconds each. The homogenate is first centrifuged at 2000 rpm on a tabletop low speed centrifuge for 10 minutes. The supernatant, after passing through a cell strainer, is then re-centrifuged at 50,000×g for 25 minutes at 4° C. The pellet is resuspended into buffer B (15% glycerol, 20 mM HEPES, pH 7.4, 0.1 mM EDTA, EDTA-free complete protease inhibitor cocktail [1 tablet/10 ml]). Protein concentration of the preparation is determined using the BCA Protein Assay kit (Pierce) using BSA as standard. The membranes are aliquoted and kept frozen at −80° C.

Solutions of test compounds ranging from 10 mM to 0.01 nM are prepared in DMSO. S1P is diluted in 4% BSA solution as positive controls. The desired amount of membrane preparation is diluted with ice-cold assay buffer (20 mM HEPES, pH 7.4, 100 mM NaCl, 10 mM $MgCl_2$, 0.1% Fatty acid-free BSA, 5 µM GDP) and vortexed well. 2 µl or less of compound is distributed into each well of a round-bottom 96-well polystyrene assay plate, followed by addition of 100 µl of diluted membranes (3-10 µg/well) and kept on ice until the addition of hot GTPγS. [$^{35}S$]-GTPγS is diluted 1:1000 (v/v) with cold assay buffer and 100 µl is added into each well. The reaction is carried out at room temperature for 90 minutes before the membranes are harvested onto Perkin-Elmer Unifilter® GF/B-96 filter plate using a Packard Filtermate Harvester. After several washes with wash buffer (20 mM HEPES, pH 7.4, 100 mM NaCl, 10 mM $MgCl_2$), and a rinse with 95% ethanol, the filter is dried in a 37° C. oven for 30 minutes. MicroScint-20 is added and the plate sealed for scintillation counting on TopCount. $EC_{50}$ values are obtained by fitting the GTP [γ-$^{35}S$] binding curves (raw data) with the dose response curve-fitting tool of GraphPad Prism. Six or twelve different concentrations are used to generate a concentration response curve (using three data points per concentration).

S1P 3, -4, -5 and -6 GTP [γ-$^{35}S$] binding assays are carried out in a comparable manner to the S1P1 GTP [γ-$^{35}S$] binding assay using membranes from CHO cells stably expressing c-terminal c-myc tagged or untagged receptors. For each membrane preparation, titration experiments are first run with S1P control to determine the optimal amount of membranes to be added per assay well.

Compounds of formula I are tested according to the above assay and are observed to exhibit selectivity for the S1P1 receptor. For example, Compounds of Examples 4, 13 and 21 have an $EC_{50}$<1 µM in the above assay and are e.g. at least 20 fold selective for S1P1 compared to S1P3, and e.g. at least 20 fold selective for S1P1 compared to S1P5.

B. In vitro: FLIPR Calcium Flux Assay

Compounds of the invention are tested for agonist activity on S1P1, S1P3, S1P5, and S1P6 with a FLIPR calcium flux assay. Briefly, CHO cells expressing an S1P receptor are maintained in F-12K medium (ATCC), containing 5% FBS, with 500 µg/ml of G418. Prior to the assay, the cells are plated in 384 black clear bottom plates at the density of 10,000 cells/well/25 µl, in the medium of F-12K containing 1% FBS. The second day, the cells are washed three times (25 µl/each) with washing buffer. About 25 µl of dye are added to each well and incubated for 1 hour at 37° C. and 5% $CO_2$. The cells are then washed four times with washing buffer (25 µl/each). The calcium flux is assayed after adding 25 µl of SEW2871 (published by Rosen et al., used as reference) solution to each well of cells. The same assay is performed with cells expressing each of the different S1P receptors. Titration in the FLIPR calcium flux assay is recorded over a 3-minute interval, and quantitated as maximal peak height percentage response relative to S1P-1 activation. The compounds of the invention are active in this assay at a concentration of from $10^{-12}$ and $3.10^{-5}$ nM.

C. In vivo: Screening Assays for Measurement of Blood Lymphocyte Depletion

Measurement of circulating lymphocytes: Compounds to be tested are dissolved in DMSO/PEG200 and further diluted with deionized water. Rats (Lewis strain, female, 6-12 weeks old) are administered 1 mg/kg of compound to be tested in 4 ml/kg vehicle (max. 2% DMSO/max. 2% PEG200/water) via per os application. DMSO/PEG200/water and FTY720 (0.3 mg/kg) are included as negative and positive controls, respectively.

Blood is collected from the sublingual vein 2, 6, 24 and 48 hours after administration under short isoflurane anesthesia. Whole blood samples are subjected to hematology analysis. Peripheral lymphocyte counts are determined using an automated analyzer. Subpopulations of peripheral blood lymphocytes are stained by fluorochrome-conjugated specific antibodies and analyzed using a fluorescent activating cell sorter (Facscalibur). Two rats are used to assess the lymphocyte depletion activity of each compound screened. The result is an $ED_{50}$, which is defined as the effective dose required to display 50% of blood lymphocyte depletion. Compounds of formula I are tested according to the above assay and have an $ED_{50}$ of less than 10 mg/kg.

The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves opthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 5.0 mg/kg per body weight. An indicated daily dosage in the larger mammal, e.g. humans, is in the range from about 0.5 mg to about 500 mg, conveniently administered, for example, in divided doses up to four times a day or in retard form. Suitable unit dosage forms for oral administration comprise from ca. 0.1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, AP23464, AP23675, AP23841, TAFA-93, biolimus-7 or biolimus-9; an ascomycin having immunosuppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-oxo-propionitrile, in free form or in a pharmaceutically acceptable salt form, e.g. mono-citrate (also called CP-690,550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4lg (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

Where the compounds of formula I are administered in conjunction with other immunosuppressive/immunomodulatory, anti-inflammatory. chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:

1. A compound of formula I:

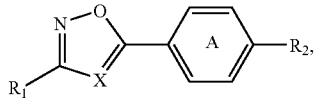

wherein
X is —N= or =CH—;
R$_1$ is biphenylyl, 4-phenoxyphenyl or 4-(phenyl-C$_1$-C$_4$-alkoxy)-phenyl, where at least one of the phenyl groups bears a halo-C$_{1-4}$-alkyl; or is phenyl substituted by C$_{3-6}$-cycloalkyl and halo-C$_{1-8}$-alkyl in the meta and para positions or vice versa;
R$_2$ is C$_{1-4}$-alkyl optionally substituted by halogen, OH, NH$_2$, C$_{1-4}$-alkoxy or C$_{1-4}$-alkylcarbonyloxy; or is amino; OH; C$_{1-4}$-alkoxy; NH—OH; carboxy; sulfamoyl; carbamoyl; or HN—CO—C$_{1-4}$-alkyl; or
R$_2$ is R$_3$-R$_4$—COOH or R$_3$-R$_4$—CONH$_2$, where R$_3$ is SO$_2$—NH, SO$_2$—N(C$_{1-4}$-alkyl), CO—NH, CO—N(C$_{1-4}$-alkyl), CH$_2$—O, NH—CO, or N(C$_{1-4}$-alkyl)CO, and R$_4$ is C$_{1-6}$-alkylene optionally interrupted by O; and
Ring A is phenyl optionally further substituted by halogen, C$_{1-4}$-alkyl, halo-C$_{1-4}$-alkyl, C$_{1-4}$-alkoxy, halo-C$_{1-4}$-alkoxy or nitrile,
or a salt thereof.

2. The compound according to claim 1, wherein
R$_1$ is biphenylyl, where at least one of the phenyl groups bears a halo-C$_{1-4}$-alkyl; or is phenyl substituted by halo-C$_{1-8}$-alkyl and C$_{3-6}$-cycloalkyl in the para and meta positions or vice versa,
or a salt thereof.

3. The compound according to claim 1, wherein
R$_1$ is biphenylyl, where at least one of the phenyl groups bears a halo-C$_{1-4}$-alkyl; or is phenyl substituted by C$_{3-6}$-cycloalkyl and halo-C$_{1-8}$-alkyl in the meta position and the para position or vice versa; and
R$_2$ is R$_3$-R$_4$—COOH or R$_3$-R$_4$—CONH$_2$, where R$_3$ is SO$_2$—NH, SO$_2$—N(C$_{1-4}$-alkyl), CO—NH, CO—N(C$_{1-4}$-alkyl), CH$_2$—O, NH—CO, or N(C$_{1-4}$-alkyl)CO, and R$_4$ is C$_{1-6}$-alkylene optionally interrupted by O;
or a salt thereof.

4. A process for the preparation of a compound of formula I,

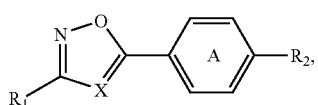

which process comprises
(i) for the production of a compound of formula I, wherein X is —N= and R$_2$ is C$_{1-4}$-alkyl optionally substituted by halogen, OH, NH$_2$, C$_{1-4}$-alkoxy or C$_{1-4}$-alkylcarbonyloxy; or is amino; OH; C$_{1-4}$-alkoxy; NH—OH; carboxy; sulfamoyl; carbamoyl; or HN—CO—C$_{1-4}$-alkyl; or is R$_3$-R$_4$—COOH or R$_3$-R$_4$—CONH$_2$, where R$_3$ is SO$_2$—NH, SO$_2$—N(C$_{1-4}$-alkyl), CO—NH, CO—N(C$_{1-4}$-alkyl), CH$_2$—O, NH—CO, or N(C$_{1-4}$-alkyl)CO, and R$_4$ is C$_{1-6}$-alkylene optionally interrupted by O, reacting a compound of formula II

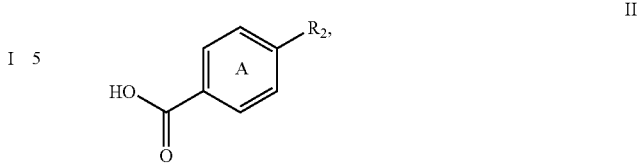

wherein ring A is phenyl optionally further substituted by halogen, C$_{1-4}$-alkyl, halo-C$_{1-4}$-alkyl, C$_{1-4}$-alkoxy, halo-C$_{1-4}$-alkoxy or nitrile, and R$_2$ is as defined above, or a functional derivative thereof, with a compound of formula III

wherein R$_1$ is biphenylyl, 4-phenoxyphenyl or 4-(phenyl-C$_1$-C$_4$-alkoxy)-phenyl, where at least one of the phenyl groups bears a halo-C$_{1-4}$-alkyl; or is phenyl substituted by C$_{3-6}$-cycloalkyl and halo-C$_{1-8}$-alkyl in the meta and para positions or vice versa, or a functional derivative thereof; or
(ii) for the production of a compound of formula I, wherein X is CH and R$_2$ is NH$_2$, reacting a compound of formula VI

wherein R$_1$ is as defined above,
with a compound of formula VII

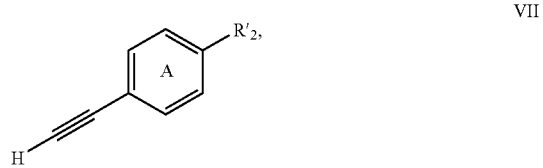

wherein Ring A is as defined above and R$_2$' is NH$_2$;
and recovering either resulting compound of formula I in free form or in salt form, and, where required, converting the compound of formula I obtained in free form into the desired salt form or vice versa.

5. A pharmaceutical composition comprising a compound according to claim 1 in free form or pharmaceutically-acceptable salt form in association with a pharmaceutically-acceptable diluent or carrier therefor.

6. A pharmaceutical combination, comprising a) a first agent which is a compound according to claim 1, in free form or in pharmaceutically-acceptable salt form, and b) at least one co-agent that is an immunosuppressant, immunomodulatory, anti-inflammatory, chemotherapeutic or anti-infectious agent.

7. The compound according to claim 1 that is 3-{4-[3-(2-trifluoromethyl-biphenyl-4-yl)-[1,2,4]oxadiazol-5-yl]-benzenesulfonylamino}-propionic acid, or a salt thereof.

* * * * *